United States Patent [19]

Wahlig et al.

[11] Patent Number: 4,853,225

[45] Date of Patent: Aug. 1, 1989

[54] PROCESS FOR IMPLANTING A MEDICAMENT DEPOT

[75] Inventors: Helmut Wahlig, Darmstadt; Elvira Dingeldein, Dreieich; Johannes Rothe, Rossdorf; Wolfgang Stille, Frankfurt, all of Fed. Rep. of Germany

[73] Assignee: Merck Patent Gesellschaft Mit Beschrankter Haftung, Darmstadt, Fed. Rep. of Germany

[21] Appl. No.: 938,200

[22] Filed: Dec. 5, 1986

[30] Foreign Application Priority Data

Dec. 5, 1985 [DE] Fed. Rep. of Germany ....... 3542972

[51] Int. Cl.⁴ ............................................... A61F 2/00
[52] U.S. Cl. .................................... 424/423; 424/424; 424/425; 424/426; 623/11; 623/16
[58] Field of Search ............... 424/423, 424, 425, 426, 424/422; 623/11, 16

[56] References Cited

U.S. PATENT DOCUMENTS

| 3,857,932 | 12/1974 | Sheperd et al. | 424/487 X |
| 3,882,858 | 5/1975 | Klemm | 128/92 G |
| 4,191,740 | 3/1980 | Heusser et al. | 424/14 |
| 4,203,442 | 5/1980 | Michaels | 128/260 |
| 4,291,013 | 9/1981 | Wahlig et al. | 424/16 |
| 4,293,539 | 10/1981 | Ludwig et al. | 424/19 |
| 4,322,398 | 3/1982 | Reiner et al. | 424/19 |
| 4,357,312 | 11/1982 | Hsieh et al. | 424/425 |
| 4,563,485 | 1/1986 | Fox, Jr. et al. | 424/423 X |
| 4,595,713 | 6/1986 | St. John | 424/423 X |
| 4,617,293 | 10/1986 | Wahlig et al. | 514/41 |
| 4,619,913 | 10/1986 | Luck et al. | 514/2 |

FOREIGN PATENT DOCUMENTS 2093348 9/0282 United Kingdom ................ 424/426

OTHER PUBLICATIONS

Smith, J. T. *Chemistry and Mode of Action of 4-Quinolone Agents* FAC., vol. 3-5, pp. 493-508, (1984).
Wolfson, J. S. et al., *The Fluoroquinolones* Antimicrobial Agents and Chemotherapy, vol. 28, No. 4, pp. 581-586, (Oct. 1985).

Primary Examiner—Thurman K. Page
Attorney, Agent, or Firm—Millen, White & Zelano

[57] ABSTRACT

The invention relates to an implantable medicament depot comprising physiologically acceptable excipients and at least one delayed release active compound which is a chemotherapeutic of the gyrase inhibitor type.

The depot can be used for combating infections.

13 Claims, No Drawings

PROCESS FOR IMPLANTING A MEDICAMENT DEPOT

This invention relates to a new implantable medicament.

SUMMARY OF THE INVENTION

It is an object of this invention to provide a new implantable medicament having valuable properties.

Upon further study of the specification and appended claims, further objects and advantages of this invention will become apparent to those skilled in the art.

These objects have been achieved by this invention by providing an implantable medicament depot comprising, and preferably consisting essentially of, physiologically acceptable excipients which achieve a delayed release of an active agent and at least one active compound for delayed release, and containing a chemotherapeutic of the gyrase inhibitor type as the active compound.

The invention furthermore relates to the use of gyrase inhibitors as chemotherapeutic active compounds in implantable medicament depots and to methods of using these depots to treat indications.

Preferred excipients are plastics, especially thermoplastic plastics, above all polymers, in particular those based on polyacrylates, and/or polymethacrylates, tricalcium phosphate and hydroxyapatite, and furthermore collagen and polysaccharides which are capable of gelling, such as agarose, gelatine, fibrin, lactide, glycolide and/or lactide/glycolide.

Medicament depots which contain these excipients and, preferably, antibiotics as active compounds are described, for example, in German Offenlegungsschriften Nos. 2,320,373, 2,651,441, 2,657,370, 2,843,963, 2,935,194, 3,206,725, 3,206,726 and 3,334,595 and in the literature mentioned therein. This prior art is expressly incorporated by reference for details of the preparation and composition of the medicament depots.

The expression "medicament depot" as used here has a broad meaning; it encompasses not only the usual depot formulations but also implants furnished with gyrase inhibitors, for example, artificial organs, parts of bones and teeth, tooth fillings, joints, bone pins and screws, osteosynthesis plates, catheters, probes, pacemaker cases, etc. The active agents can also be applied to the surfaces of these objects in the form of coatings (films) or gels, e.g., by dipping or spraying. Occlusive foils containing gyrase inhibirots are also included in the expression "medicament depot," particularly plasters.

A large number of chemotherapeutics of the gyrase inhibitor ("quinolones") type are known. All gyrase inhibitors are in principle suitable for the purpose according to this invention. Chemistry and mode of action of some of these compounds are described by I.T. Smith in FAC FOrtschritte der antimikrobiellen und antineoplastischen Chemotherapie, Vol. 3-5, 1984, pages 493-508. Another review by John S. Wolfson and David C. Hooper can be found in Antimicrobial Agents and Chemotherapy, Oct. 1985, pages 581-596.

Preferred gyrase inhibitors correspond to the formula I

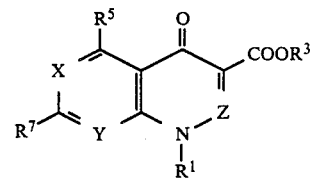

wherein
 X is N or $CR^6$,
 Y is N or $CR^8$,
 Z is N or CH,
 $R^1$ is alkyl, alkenyl, hydroxyalkyl, Hal-alkyl, $NR^9R^{10}$, $OR^{11}$, cyclo-alkyl, Ar or Ar-alkyl,
 $R^3$ is H or alkyl,
 $R^5$ is H, Hal, alkyl or alkoxy,
 $R^6$ is H, Hal, alkyl, alkoxy or $NO_2$,
 $R^7$ is alkyl, Hal, $NR^9r^{10}$ or a 5- or 6-membered N-containing saturated or unsaturated heterocyclic radical, which can also contain a further hetero atom and/or can be substituted, or
 $R^6$ and $R^7$ together are also methylenedioxy,
 $R^8$ is H, Hal, alkyl or alkoxy, or
 $R^8$ and $R^1$ together are also $-O-CH_2-$CHalkyl or $-CH_2CH_2-$CHalkyl,
 $R^9$, $R^{10}$ and $R^{11}$ are each H or alkyl,
 Ar is an unsubstituted or substituted phenyl group and
 Hal is F, Cl, Br or I, and
 the alkyl, alkenyl and alkoxy groups in each case contain up to 6 C atoms as do the cycloalkyl groups.

Compounds of the formulae Ia to Ic which correspond to the formula I but wherein,
in Ia
 Y is N or $CR^8$,
 Z is N or CH,
 $R^1$ is alkyl, Hal-alkyl, NH-alkyl, O-alkyl, cyclo-alkyl or Hal-phenyl,
 $R^3$ is H,
 $R^5$ is H,
 $R^6$ is H or Hal,
 $R^7$ is alkyl, Hal or a 5- or 6-membered N-containing saturated or unsaturated heterocyclic radical which can contain a further N atom and/or can be substituted by one or two alkyl, amino or alkylaminoalkyl group(s), or
 $R^6$ and $R^7$ together are also methylenedioxy,
 $R^8$ is H, Hal, or alkyl, or
 $R^8$ and $R^1$ together are also $-O-CH_2-$CHalkyl or $-CH_2CH_2-$CHalkyl and
 Hal is F or Cl and
 the alkyl groups in each case contain 1-3 C atoms;
in Ib
 Y is N or $CR^8$,
 Z is N or CH,
 $R^1$ is alkyl, 2-fluoroethyl, methylamino, methoxy, cyclopropyl or p-fluorophenyl,
 $R^3$ and $R^5$ are each H,
 $R^6$ is H or F,
 $R^7$ is methyl, Cl, pyrryl, pyrrolidino, 3,4-dimethylpyrrolidino, 3-aminopyrrolidino, 3-amino-4-methylpyrrolidino, 3-ethylaminomethyl-pyrrolidino, pyridyl, piperidyl, piperazino or 3- or 4-methylpiperazine, or
 $R^6$ and $R^7$ together are also methylenedioxy and $R^8$ is H, methyl or F, or $R^8$ and $R^1$ together are also —OCH$_2$—CH(CH$_3$)—or —CH$_2$CH$_2$—CH(CH$_3$)— and the alkyl groups in each case contain 1-3 C atoms, and in Ic Y is N or CR$^8$, Z is N or CH, $R^1$ is ethyl or cyclopropyl, $R^3$ and $R^5$ are each H, $R^6$ is F, $R^7$ is piperazino or 3- or 4-methylpiperazino, and $R^8$ is H, or $R^8$ and $R^1$ together are also —O—CH$_2$—CH(CH$_3$)—, are particularly preferred.

Suitable substituents on the phenyl group include those mentioned above for $R^7$-hetero groups. The hetero groups can be aromatic or saturated and unsaturated aliphatic groups, with the additional hetero atom being O, S or N.

Preferred gyrase inhibitors are, specifically ciprofloxacin and ofloxacin, and furthermore amifloxacin, cinoxacin, difloxacin (A-56619), enoxacin, flumequin, irloxacin, miloxacin, nalidixic acid, norfloxacin, oxolic acid, pefloxacin, pipemidic acid, piromidic acid, rosoxacin, A-56620, A-57132, A-60969, A-656619, A-656620, Am-833, AT-3295, AT-3765, CI-934, E-3432, E-3499, EN-272, NY-198, OPC-7594, Ro-23-6240, S-25930, S-25932, T-14097, 79286-76-3 and 80-107118, furthermore 1-ethyl-2-phenyl-4-pyridone-5-carboxylic acid and its derivatives substituted in the phenyl ring.

The medicament depots preferably contain 0.01 to 10, in particular 0.1 to 3 and above all 0.1 to 1% of the chemotherapeutic agent.

Medicament depots based on polyacrylates and/or polymethacrylates are particularly preferred. They can be prepared, for example, analogously to the statements in German Offenlegungsschriften 2,320,373 and 2,651,441, by mixing about 50 to 75 parts by weight of a fine-particled polymer of acrylic and/or methacrylic acid esters, which can optionally contain other additives, for example X-ray contrast agents, such as ZrO$_2$, dyestuffs, such as chlorophyll, and/or catalysts, 0.01 to 10 parts by weight of the chemotherapeutic and 20 to 45 parts by weight of an acrylic and/or methacrylic acid ester, which optionally contains further additives, for example stabilizers and/or polymerization accelerators, to form a semisolid paste, bringing this into the desired shape and allowing it to harden by polymerization and crosslinking. If desired, the mixture can additionally contain one or more physiologically acceptable amino acids, preferably in an amount of 1 to 15 parts by weight. An additional content of preferably naturally occurring amino acids, for example glycine, alanine, leucine, threonine, valine, serine, hydroxyproline, proline, histidine and/or arginine, can promote reliable release of the active compound.

The materials of plastic based on polyacrylates and/or polymethacrylates which can be used as starting materials are known per se. A bone cement, for example, which contains in a normal pack 2 sachets each containing about 40 g of powder and 2 ampoules each containing 20 ml of liquid is very useful. The powder is a fine bead polymer of methyl methacrylate with a copolymer content of methyl acrylate. About 0.5% of dibenzoyl peroxide is added to the powder as the catalyst. For identification of the material, traces of chlorophyll are copolymerized in during the preparation. If appropriate, the powder can additionally contain, for example, zirconium dioxide, as an X-ray contrast agent. The associated liquid consists of monomeric methyl methacrylate, to which about 0.7% of dimethyl-p-toluidine is added as a polymerization accelerator and traces of hydroquinone are added as the stabilizer. This liquid is also as a rule colored with traces of chlorophyll for identification. The powder, packaged in polyethylene sachets, is sterilized with ethylene oxide. The liquid is sterile-filtered and filled into glass ampoules.

When two parts by weight of powder are mixed together with one part by weight of liquid, the dibenzoyl peroxide reacts with the dimethyl-p-toluidine in the liquid, whereupon free radical polymerization is initiated. The mixture is calculated so that it can be used as a dough-like paste after only about one minute. This paste remains kneadable for several minutes and then starts to harden, with evolution of heat. After about 5 to 10 minutes, the polymerization has essentially ended. During the polymerization, as long as the paste can still be shaped, this can be brought into any desired shape, that is to say, for example, can be introduced directly into the body for filling bone cavities or for cementing in prostheses or can be used to produce shaped articles with harden outside the body and can then be used at any desired positions in the body.

The chemotherapeutic and/or the amino acid can be mixed with the other constituents as a fine powder and can thus be distributed homogeneously in the polymer formed. However, during preparation of the prepolymer, it can also already be incorporated into this.

The medicament depot according to the invention can be polymerized ready for use and thus provided in a predetermined shape. This is the case, in particular, if, for example, only the function of a local source of active compound must be met for use in soft parts. For this, the depot can be produced in any desired shape, for example as granules, as a cube, sphere or ellipsoid or as a film, sheet, pin, tube, fibre, filament, network or fabric or in another shape suitable for the particular use.

It is also possible, however, to provide the surgeon with the material according to the invention as a precursor, so that shaping takes place only on implantation and the medicament depot can be fitted to the local circumstances in an optimum manner and the material can also be used as a conventional bone cement for implanation of prostheses. For these, the constituents can be packaged ready-for-use analogously to the known bone cements described above, so that amounts of the solids and the liquid (of the monomer) which match one another are present in one pack. The medicament depot can then be produced from this precursor in a simple manner by mixing the components; the polymerization of the monomer is thereby started by the added catalyst, and after a reaction time of a few minutes the hardened end product is obtained. In the intermediate period in which the material has plastic deformability, it can be introduced into the body and thereby shaped.

Medicament depots based on tricalcium phosphate can be prepared, for example, according to German Offenlegungsschrift 2,807,132 or German Offenlegungsschrift 3,206,726. Thus, pulverulent tricalcium phosphate can be compressed with the chemotherapeutic either directly or with the addition of about 1–20% of a physiologically acceptable binder which can preferably be absorbed in the body, for example a collagen degradation product, elastin or, preferably, calcium sulfate, to form a medicament depot which, after implantation, initially retains its shape and releases the active compound in a protracted manner, but in the long term is absorbed into the body. However, it is also possible to charge granules of tricalcium phosphate, preferably those with particle sizes of between 0.1 to 8 mm, preferably between 1.4 and 2.8 mm, and pore volumes of between 40 and 90, preferably 60 and 80%, with the chemotherapeutics.

"Tricalcium phosphate" in the context of the present invention includes not only pure tricalcium phosphates, such as α- or β-whitlockite, but also apatites, hydroxyapatites (durapatites) or phosphorite and similar substances, which can be described only approximately by the formula $Ca_3(PO_4)_2$ or $Ca_5(PO_4)_3OH$. The tricalcium phosphate should in all cases be absorbable in the body and is preferably employed in powder form, advantageously with particle sizes of about 0.5 to about 50 μm, preferably about 0.5 to about 20 μm.

Medicament depots based on tricalcium phosphate can be prepared, for example, by compressing the constitutents under pressures of about 5 to about 1,200, preferably 100 to 800 bar at temperatures between about 20 and about 150° C., and in particular in any desired shapes, for example those mentioned above.

Medicament depots based on collagen can be prepared, for example, analogously to the statements in German Offenlegungsschriften 2,843,963 or 3,334,595.

Collegans in which the pore structure of the natural material is retained and which have pore volumes of about 60 to about 95% are preferred. Reconstituted collagens with a fabric or sponge structure are furthermore preferred, especially those which consist of fibers not more than 10mm in length and/or in which the polypeptide chains are additionally crosslinked, for example with formaldehyde, glutardialdehyde, glyoxal or hexamethylene diisocyanate.

Depots based on collagen advantageously contain in addition bioabsorbable binderes, such as glycolidelactide copolymers, and/or bioabsorbable polymers, for example acid polysaccharides, such as pectic acids or alginic acids and/or salts thereof and/or calcium phosphate. They can be prepared by compressing the constituents at temperatures between about 20 and about 200° C., preferably between 70° and 150°, under pressures between about 300 and about 1,200, preferably between 500 and 800 bar. Depots based on a collagen with a retained pore structure are obtainable, for example, by impregnating the collagen matrix with a solution of a salt of the chemotherapeutic and a salt of the acid polysaccharide and then shifting the pH into a range from pH 4 to 8. Depots based on a reconstituted collagen with its natural molecular structure largely retained can be prepared, for example, by adding the chemotherapeutic and an acid polysaccharide to a suspension of such a collagen, the pH value of the suspension being adjusted to a value below 7 before or after the addition and the suspension subsequently being freeze-dried, if appropriate after pouring into molds. Fabric-like or spongey-porous shaped articles can also first be prepared from reconstituted collagen fibers and are then impregnated with a solution of the chemotherapeutic and the polysaccharide, the pH value of the immersion solution is subsequently adjusted to below 7 and the shaped articles charged with active compound are freezedried.

Medicament depots based on polysaccharides which are capable of gelling, in particular agarose and/or gelatine, can be prepared analogously to the statements in German Offenlegungsschrift 2,657,370. The chemotherapeutic is advantageously incorporated into a solution which has been obtained from physiological saline solution and the polysaccharide and to which a substance which promotes diffusion in tissue, such as hyaluronidase, can advantageously be added, as well as substances which promote bone growth, such as calcium phosphate and/or other active compounds. Such products can be kept in the liquid state at a temperature above body temperature; on cooling to body temperature they form stable gels.

Medicaments depots based on fibrin are preferably likewise present in the form of gels and can be prepared, for example, analogously to the statements in German Offenlegungsschrift 3,206,725, advantageously by mixing a fibrinogen solution, a thrombin solution and the chemotherapeutic. The fibrin is thereby precipitated. The thrombin solution advantageously additionally contains aprotinin and/or is enriched with calcium ions, for example in the form of $CaCl_2$. It is also possible for the gel to be formed only at the chosen place, for example immediately in the bone cavity, by addition of the thrombin solution to the fibrinogen solution, the chemotherapeutic, advantageously in the form of a salt, being added either to the thrombin solution or to the fibrinogen solution. Preferably, however, the gel is produced by mixing the constituents outside the body.

It may be advantageous for other active compounds with different types of action additionally to be added to the medicament depot, in particular antibiotics and/or antiseptics, to increase or complement the action of the chemotherapeutic. Antibiotics should as far as possible be active against both Gram-positive and Gram-negative pathogens, and should cause no resistance or only a delayed resistance in pathogens. Examples which may be mentioned of suitable active compounds are aminoglycoside antibiotics, such as amikacin, butirosin, dideoxykanamycin B (DKP), fortimycin, gentamycin, kanamycin, lividomycin, neomycin, netilmicin, ribostamycin, sagamycins, seldomycins and eipmers thereof, sisomicin, sorbistin, tobramycin, streptomycins, lincomycins, such as clindamycin, lincomycin and rifamycins, such as rifampicin and rifamycin. Possible antiseptics are, for example, bromochlorophene, hexetidine, buclosamide, salicyclic acid, cerium nitrate, chlorhexidine, 5-chloro-8-hydroxy-quinoline, copper 8-hydroxyquinolate, acridine orange, undecenoic acid, undecoylium chloride, silver salts, such as silver sulfadiazine, mafenide, nitrofurazole, cloflucarban, tribromsalan, taurolin and noxythiolin. Combinations with other active compounds, for example cytostatics, such as methoxtrexate, cisplatin, adriamycin, vinblastin and/or anti-inflammatory agents are furthermore possible. These additional active compounds, the nature and amount of which depend on the desired additional action, can also be mixed with the other materials in a manner which is customary per se, preferably in finely divided powder form, it also being possible here, if appropriate, for them to be premixed with individual members of the other constitutents or incorporated into the prepolymer.

The medicament depots according to the invention can be used in therapy, in particular for combating infections, with gram-positive or gram-negative bacterial such as *Acinetobacter anitratus, Aeromonas hydrophila, Bacillus fragilis, Bacillus subtilis, Branhamella catarrhalis, Campylobacter jejuni, Chlamydia trachomatis,* Citrobacter spp. such as *Citrobacter diversus, Cit-*

*robacter freundii,* Clostridium spp, such as *Clostridium perfringens, Enterobacter aerogenes, Enterobacter agglomerans, Enterobacter cloacae, Escherichia coli, Gardnerella vaginalis, Haemophilus influenzae, Klebsiella oxytoca, Klebsiella pneumoniae, Legionella pneumophila, Morganella morgani, Mycobacterium tuberculosis, Mycoplasma hominis, Mycoplasma pneumoniae, Neisseria gonorrhoeae, Neisseria meningitidis, Pasteurella multocida, Peptococci, Peptostreptococci, Proteus mirabilis, Proteus vulgaris, Providencia rettgeri, Providencia stuartii, Pseudomonas aeruginosa, Pseudomonas cepacia, Pseudomonas maltophila, Pseudomonas stuartii,* Salmonella spp. such as *Salmonella newport, Salmonella typhimurium, Serratia marcescens,* Shigella spp. such as *Shigella dysenteriae,* Staphylococcus spp. such as *Staphylococcus aureus, Staphylococcus saprophyticus, Streptococcus agalactiae, Streptococcus faecalis, Streptococcus haemolyticus, Streptococcus pneumoniae, Streptococcus pyogenes, Streptococcus viridans, Ureaplasma urealyticum,* Vibrio spp., *Yersinia enterocolitica.*

The depots of this invention can be administered for these conventional indications analogously to the known agents described, preferably f.e., in U.S. Pat. Nos. 3,882,858 or 4,191,740, furthermore 4,291,013 or 4,617,293. The unit dosage ranges mentioned above are applicable to these conventional treatments. Particularly important is the prevention of bone and soft tissue infections in the human body.

All the references mentioned above and below are incorparated entirely by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight, unless otherwise indicated.

EXAMPLES

Example 1

40 g of a sterile fine bead polymer consisting of a copolymer of methyl acrylate and methyl methacrylate and additionally containing 0.5% of dibenzoyl peroxide, traces of chlorophyll and 15% of zirconium dioxide as an X-ray contrast agent, are mixed thoroughly with 0.5 g of cirpofloxacin. The resulting powder is then mixed with 20 ml of a liquid consisting of monomeric methyl methacrylate with the addition of about 0.7% of dimethyl-p-toluidine and about 0.006% of hydroquinone. Small beads with a diameter of about 7 mm are shaped from the paste formed after thorough mixing. After about 6 minutes, the particles have hardened. If appropriate, this procedure can be followed by sterilization, for example by gassing with ethylene oxide. The small beads can then be used to fill osteomyelitic cavities.

Example 2

Small beads with a diameter of about 7–10 mm are shaped analogously to Example 1. The addition of ciprofloxacin is 1 g per 60 g of polymer. Before they have hardened completely, the resulting particles are threaded like beads, at a distance of about 2 mm, onto a thread (surgical high-alloy steel wire) with a diameter of about 0.1 mm. The small beads are allowed to harden in this state. During filling of osteomyelitic cavities, the "string of beads" can be cut to any desired length.

Example 3

Granules consisting of particles with an average diameter of 6 to 8 mm are prepared analogously to Example 1. Before the polymerization, 0.5 g of gentamycin sulfate and 1 g of ciprofloxacin are added. The resulting product is used to fill osteomyelitic cavities.

Example 4

Analogously to Example 1, 0.8 g of ofloxacin is added to 40 g of the bead polymer. Polymerization is carried out after addition of 20 ml of the liquid containing the monomer. Small beads with a diamter of 7 to 10 mm are shaped. These can be threaded onto a flexible surgical wire analogously to Example 2, which facilitates handling during the operation.

Example 5

The procedure followed is analogous to Example 1, but 0.4 g of glycine is also added to the powder mixture. Mixing of the resulting powder with the monomeric methyl methacrylate gives a paste which can be introduced or forced into a bone cavity manually or with the aid of a gun and is left to harden there. A prosthesis, such as, for example, an endoprosthesis, can be pressed into the paste which has been introduced into the body and has not yet hardened. After hardening of the plastic, the prosthesis is firmly anchored in the body.

Example 6

36 g of a fine-particled copolymer of methyl acrylate and methyl methacrylate which additionally contains 0.5% of dibenzoyl peroxide and traces of chlorophyll, 4% of micronized L-arginine, 0.5 g of ciprofloxacin, 0.5 g of gentamycin and 20 ml of methyl methacrylate which contains about 0.7% of dimethyl-p-toluidine and about 0.006% of hydroquinone are mixed thoroughly. Beads, pins, ovoids and larger implants, such as cylinders, tubes, sheets, films and other particles of any desired shape and size are shaped from the paste formed and have hardened after a few minutes. The particles are packaged under sterile conditions and can be used as local active compound depots.

Example 7

3 g of ciprofloxacin and 3 g of penta-calcium hydroxide triphosphate are mixed and the mixture is compressed to tablets with a tablet press at 20° under a pressing pressure of about 100 bar.

Example 8

3 g of ciprofloxacin, 3 g of tricalcium phosphate and 0.3 g of calcium sulfate are mixed and the mixture is pressed to tablets at 20° under a compression pressure of about 100 bar.

Example 9

3 g of ciprofloxacin, 3 g of hydroxyapatite and 1 g of protein powder are mixed and the mixture is compressed to tablets at 80° under a compression pressure of about 100 bar.

Example 10

A mixture of 475 g of finely ground collagen, 25 g of a copolymer of 80 mol per cent of L-lactide and 20 mol per cent of glycolide with a reduced specific viscosity of 42 cm$^3$/g and 10 g of ciprofloxacin is homogenized and then compressed to tablets in a metallic negative mold in a heated press at 135° under about 630 bar for one minute (diameter 1 cm, height 2 mm).

If desired, the procedure can be followed by sterilization by gassing with ethylene oxide or by irradiation. The tablets can be used for prophylaxis of infection in soft-tissue wounds or debris zones in cases of open bone fracturess or for filling osteomyelitic cavities.

Example 11

A mixture of 375 g of finely ground collagen, 25 g of copolymer of 70 mol per cent of L-lactide and 30 mol per cent of glycolide with a reduced specific viscosity of 53 cm$^3$/g, 100 g of powdered tricalcium phosphate and 10 g of norfloxacin is homogenized and then shaped, in an extruder at a material temperature of about 145°, to a strand 1.5 mm in diameter, which is then reduced to granules at spacings of 1 mm.

Example 12

A mixture of 25 g of protein powder (hydrolized water-soluble collagen; average molecular weight about 3,000), 10 g of ofloxacin and 100 g of powdered tricalcium phosphate is compressed at 90° under about 650 bar for two minutes. The compressed article is then ground and the resulting powder is mixed with 375 g of collagen. The mixture thus obtained is compressed to beads (diameter 6 mm) at 85° under 650 bar for one minute.

Example 13

200 ml of an aqueous solution of 1.7 g of ciprofloxacin which has been brought to pH 9 with NaOH is mixed with 200 ml of an aqueous solution of 1.7 g of the sodium salt of pectic acid (degree of esterification about 8%), which has likewise been brought to pH 9 with NaOH. 10 g of a collagen obtained by the process of German Patent 2,854,490 in the form of cuboid particles with the approximate dimensions 2×2×1 cm are introduced into this mixture. The air is removed from the porous material by evacuating and then ventilating several times. The pH value is brought to 6.5 with 1 N sulfuric acid, while stirring. The total volume is then about 500 ml. The small pieces of collagen are removed and, after dripping briefly, are frozen at −20° and then lyophilized. The active compound depot thus obtained can be packaged in sterile form by irradiation and, for example, by sealing in double-peel sachets.

Example 14

20 g of a collagen obtained by the process according to German Patent Specification 2,730,623 are suspended in 1 l of 0.5 molar acetic acid. After an equilibration time of about 12 hours, the pH value is corrected to a value between 2.5 and 3.5. The acetic acid suspension is homogenized by bringing the length of the collagen fibers to values of less than 10 mm by means of a stirrer, with simultaneous cooling. After the collagen mass thus obtained has been pressed off, it is suspended in water and pressed off again. This procedure is repeated twice more. The collagen freed from excess acetic acid is then introduced into an aqueous solution, heated at 35° and at pH 9.5, containing 1.2 g of ciprofloxacin and 1.2 g of sodium pectate in about 900 ml, with gentle stirring. After an equilibration time of 30 minutes, 1 normal sulfuric acid is added to pH 5–6 and the total volume is made up to one liter with water. The mass thus obtained is poured into prepared casting molds, shock-frozen at −20° to 40° and then freeze-dried. A flat active compound depot of a fabric-like nature which has a content of 4% of ciprofloxacin and a thickness of 2 mm to about 10 mm, corresponding to the given height of the layer of collagen slurry, is obtained. The weight per unit area is then about 40 g per m$^2$, or 200 g per m$^2$. The water uptake capacity of the active compound depot is about 2,000%, based on the dry weight.

Example 15

2 g of agarose powder are boiled with 100 ml of physiological saline solution for 30 minutes and cooled to 50°. 2 ml of the resulting sterilized solution are mixed with 150 I.U. of hyaluronidase and 10 mg of ciprofloxacin and the mixture is kept under thermostatic control at 50° until used for inserting enossal dental semi-implants.

Example 16

2 ml of the solution obtained according to Example 15 are additionally mixed with 20 mg of apatite powder. The resulting product is particularly suitable for insertion of implants.

Example 17

2 ml of the solution obtained according to Example 15 are mixed with 0.7 g of denatured bone meal. The resulting mixture is particularly useful for filling hollow cavities formed during bone operations.

Example 18

4 NIH units of thrombin (commerical product) are dissolved in 1 ml of aprotinin-calcium chloride solution (commerical product; 3,000 KIU per ml of aprotinin in 40 mmol/l CaCl$_2$), the solution is warmed to 37°, 20 mg of ciprofloxacin are added and the mixture is mixed with the same amount, first warmed to 37°, of "Fibrinkleber" (commerical product; prepared by cryoprecipitation from human donor plasma; stored at −18° or below; 1 ml of the solution contains on average 90 mg of protein which can be precipitated with thrombin, total protein content of the solution about 10%; thawed about 20–30 minutes before planned use). The mixture is allowed to solidify in cylinders of stainless steel (internal diameter 6 mm, height 10 mm) (1 ml for 3 cylinders). The gel cylinders formed are then ejected from the molds.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make numerous changes and modifications of the invention to adapt it to various usages and conditions.

What is claimed is:

1. A method of combating an infection in a patient in whom the infection already exits, comprising implanting in the patient an implantable medicament depot consisting essentially of a physiologically acceptable excipient which achieves delayed release of an active agent and an infection-treating effective amount of at least one chemotherapeutic gyrase inhibitor as the active agent for delayed release.

2. A method of claim 1, wherein the gyrase inhibitor is a compound of the formula

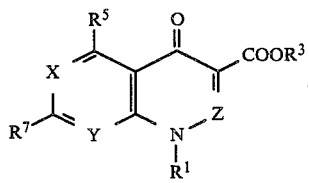

wherein
X is N or $CR^6$,
Y is N or $CR^8$,
Z is N or CH,
$R^1$ is alkyl, alkenyl, hydroxyalky, Hal-alkyl, $NR^9R^{10}$, $OR^{11}$, cycloalkyl, Ar or Ar-alkyl,
$R^3$ is H or alkyl,
$R^5$ is H, Hal, alkyl or alkoxy,
$R^6$ is H, Hal, alkyl, alkoxy or $NO_2$,
$R^7$ is alkyl, Hal, $NR^9R^{10}$, a 5- or 6-membered N-containing aromatic or aliphatic heterocycle, such as heterocycle containing an additional hetero O, N or S atom, or either of said heterocycles which is substituted, or
$R^6$ and $R^7$ together form methylenedioxy,
$R^8$ is H, Hal, alkyl or alkoxy or
$R^8$ and $R^1$ together form —O—$CH_2$—CHalkyl or —$CH_2CH_2$—CHalkyl,
$R^9$, $R^{10}$ and $R^{11}$ are each H or alkyl,
Ar is phenyl or substituted phenyl,
Hal is F, Cl, Br or I, and
the alkyl, cycloalkyl, alkenyl and alkoxy groups in each case contain up to 6 C atoms.

3. A method of claim 2 wherein
Y is N or $CR^8$,
Z is N or CH,
$R^1$ is alkyl, Hal-alkyl, NH-alkyl, O-alkyl, cycloalkyl or Hal-phenyl,
$R^3$ is H,
$R^5$ is H,
$R^6$ is H or Hal,
$R^7$ is alkyl, Hal or a 5- or 6-membered N-containing aromatic or aliphatic heterocycle which optionally can contain a further N atom, each optionally substituted by one or two alkyl, amino or alkylaminoalkyl groups, or
$R^6$ and $R^7$ together are methylenedioxy,
$R^8$ is H, Hal or alkyl, or $R^8$ and $R^1$ together are —O—$CH_2$—CHalkyl or —$CH_2CH_2$—CHalkyl and
Hal is F or Cl and
the alkyl groups in each case contain 1–3 C atoms.

4. The method of claim 2 wherein
Y is N or $CR^8$,
Z is N or CH,
$R^1$ is alkyl, 2-fluoroethyl, methylamino, methoxy, cyclopropyl or p-fluorophenyl,
$R^3$ and $R^5$ are each H,
$R^6$ is H or F,
$R^7$ is methyl, Cl, pyrrl, pyrrolidino, 3,4-dimethylpyrrolidino, 3-aminopyrrolidino, 3-amino-4-methylpyrrolidino, 3-ethylaminomethyl-pyrrolidino, pyridyl, piperidyl, piperazino or 3- or 4-methylpiperazino, or
$R^6$ and $R^7$ together are methylenedioxy and
$R^8$ is H, methyl or F, or
$R^8$ and $R^1$ together are —$OCH_2$—$CH(CH_3)$— or —$CH_2CH_2$—$CH(CH_3)$—and
the alkyl groups in each case contain 1–3 C atoms.

5. A method of claim 2 wherein
Y is N or $CR^8$
Z is N or CH,
$R^1$ is ethyl or cyclopropyl,
$R^3$ and $R^5$ are each H,
$R^6$ is F,
$R^7$ is piperazino or 3- or 4-methylpiperazino, and
$R^8$ is H, or
$R^8$ and $R^1$ together are —O—$CH_2$—$CH(CH_3)$).

6. A method of claim 1 wherein the gyrase inhibitor is ciprofloxacin, ofloxacin, amifloxacin, cinoxacin, difloxacin (A-56619), enoxacin, flumequin, irloxacin, miloxacin, malidixic acid, norfloxacin, oxolic acid, pefloxacin, pipemidic acid, piromidic acid, rosoxacin, A-56620, A-57132, A-60969, A-656619, A-656620, AM-833, AT-3295, AT-3765, CI-934, E-3432, E-3499, EN-272, NY-198, OPC-7594, Ro-23-6240, S-25930, S-25932, T-14097, 79286-76-3, 80-107118, or 1-ethyl-2-phenyl-4-pyridone-5-carboxylic acid.

7. A method of claim 1 wherein the amount of active agent is 0.01 to 10%.

8. A method of claim 1 which is an implant.

9. A method of claim 1 wherein said depot is a bone cement or bone filler.

10. A method of claim 1 wherein the excipient comprises a polyacrylate or a polymethacrylate.

11. A method of claim 1 wherein the excipient is tricalcium phosphate.

12. A method of claim 1 wherein the excipient is collagen.

13. A method of claim 1 wherein the excipient is a polysaccharide or fibrin.

* * * * *